United States Patent
Wang et al.

(10) Patent No.: US 12,370,198 B2
(45) Date of Patent: Jul. 29, 2025

(54) PHARMACEUTICAL COMPOSITIONS AND METHODS FOR TREATING PSYCHIATRIC DISORDERS

(71) Applicant: LA PHARMATECH INC., Blacksburg, VA (US)

(72) Inventors: Jianmin Wang, Pelham, AL (US); Fengming Jia, Beijing (CN); Geping Cui, Beijing (CN)

(73) Assignee: LA PHARMATECH INC, Blacksburg, VA (US)

( * ) Notice: Subject to any disclaimer, the term of this patent is extended or adjusted under 35 U.S.C. 154(b) by 0 days.

(21) Appl. No.: 19/018,731

(22) Filed: Jan. 13, 2025

(65) Prior Publication Data

US 2025/0144114 A1 May 8, 2025

Related U.S. Application Data

(63) Continuation-in-part of application No. 18/934,396, filed on Nov. 1, 2024, which is a continuation of application No. PCT/US2022/036579, filed on Jul. 8, 2022.

(51) Int. Cl.
| | |
|---|---|
| *A61K 31/5513* | (2006.01) |
| *A61K 31/445* | (2006.01) |
| *A61P 25/22* | (2006.01) |
| *A61P 25/24* | (2006.01) |

(52) U.S. Cl.
CPC ........ *A61K 31/5513* (2013.01); *A61K 31/445* (2013.01); *A61P 25/22* (2018.01); *A61P 25/24* (2018.01)

(58) Field of Classification Search
CPC ... A61K 31/5513; A61K 31/445; A61P 25/22; A61P 25/24
See application file for complete search history.

(56) References Cited

U.S. PATENT DOCUMENTS

| | | |
|---|---|---|
| 2020/0054604 A1 | 2/2020 | Zhang et al. |
| 2021/0315841 A1 | 10/2021 | Parmenter et al. |

FOREIGN PATENT DOCUMENTS

| | | |
|---|---|---|
| WO | 2024/010592 A1 | 1/2024 |

OTHER PUBLICATIONS

Van Cauwenberge P, De Belder T, Sys L. A review of the second-generation antihistamine ebastine for the treatment of allergic disorders. Expert Opin Pharmacother. Aug. 2004;5(8):1807-13.*
ISR/WO for PCT/US25/11395 mailed on May 5, 2025.

* cited by examiner

*Primary Examiner* — Sahar Javanmard
(74) *Attorney, Agent, or Firm* — Rhodes IP PLC; Christopher R Rhodes

(57) ABSTRACT

Methods of using a pharmaceutical composition comprising ebastine and alprazolam for treating patients suffering from one or more psychiatric disorders, such as major depressive disorder, generalized anxiety disorder, mild chronic depression, premenstrual dysphoric disorder are disclosed.

18 Claims, 1 Drawing Sheet

PHARMACEUTICAL COMPOSITIONS AND METHODS FOR TREATING PSYCHIATRIC DISORDERS

TECHNOLOGICAL FIELD

The invention relates to the field of practical medicine, namely, to the use of pharmaceutical compositions for treating major depressive disorder, generalized anxiety disorder, mild chronic depression, premenstrual dysphoric disorder.

SUMMARY

The invention relates to the field of practical medicine, namely, to the use of pharmaceutical compositions for alleviating manifestations of major depressive disorder, generalized anxiety disorder, mild chronic depression, premenstrual dysphoric disorder. For example, various aspects relate to use of a combination of ebastine and alprazolam to treat psychiatric disorders. Some aspects involve the use of a combination of ebastine and alprazolam to treat major depressive disorder. Other aspects involve the use of a combination of ebastine and alprazolam to treat generalized anxiety disorder. Further aspects include the use of a combination of ebastine and alprazolam to treat mild chronic depression. Some aspects include the use of a combination of ebastine and alprazolam to treat premenstrual dysphoric disorder or symptoms.

For example, various aspects relate to use of a combination of ebastine and alprazolam to treat psychiatric disorders. Some aspects involve the use of a combination of ebastine and alprazolam to treat major depressive disorder in a subject not having a sleeping disorder such as insomnia thereof. Other aspects involve the use of a combination of ebastine and alprazolam to treat generalized anxiety disorder in a subject not having a sleeping disorder such as insomnia thereof. Further aspects include the use of a combination of ebastine and alprazolam to treat mild chronic depression in a subject not having a sleeping disorder such as insomnia thereof. Some aspects include the use of a combination of ebastine and alprazolam to treat premenstrual dysphoric disorder or symptoms in a subject not having a sleeping disorder such as insomnia thereof.

In an aspect, the technology described herein is directed to pharmaceutical compositions comprising ebastine and alprazolam for use in the treatment of a psychiatric disorder. For example, the pharmaceutical composition can be used in the treatment of major depressive disorder, generalized anxiety disorder, mild chronic depression, and premenstrual dysphoric disorder and combinations thereof. The exact dosage and dosage regimen can vary from subject to subject. For example, the pharmaceutical composition can be administered to the patient in an oral solid or liquid form. The ebastine can present in the pharmaceutical composition in an amount in the range of about 10 mg to about 30 mg or in about 10 mg to about 20 mg. The alprazolam can be present in the pharmaceutical composition in an amount in the range of about 0.5 mg to about 5 mg or about 0.5 mg to about 3 mg. In some configuration, the ebastine and the alprazolam are present in the pharmaceutical composition in synergistically effective amounts.

In certain aspects, a combination of ebastine and alprazolam can be used in the treatment of psychiatric disorders where conventional antidepressants, SSRI's or mood stabilizers are not effective based on past administration of the conventional antidepressants, SSRI's or mood stabilizers on their own.

Psychiatric disorders, including major depressive disorder (MDD), generalized anxiety disorder (GAD), mild chronic depression (MCD), premenstrual dysphoric disorder (PDD), affect more than one in ten people globally (10.7%) as reported by the Institute for Health Metrics and Evaluation in their flagship Global Burden of Disease study in 2017. Two examples of psychiatric disorders, MDD and GAD, are common, severe, chronic and often life-threatening illnesses. More than 20% of the adult population suffers from these conditions at some time during their life. Suicide is estimated to be a cause of death in up to approximately 15% of individuals with MDDs. In addition, MDDs represent a major risk factor for the development of cardiovascular disease and death after myocardial infarction.

Treatments for MDD, GAD, MCD, PDD and the like include selective serotonin reuptake inhibitors (SSRIs), such as citalopram (Celexa), escitalopram oxalate (Lexapro), fluoxetine (Prozac), fluvoxamine (Luvox), paroxetine HRI (Paxil), and sertraline (Zoloft); selective serotonin & norepinephrine inhibitors (SNRIs), such as desvenlafaxine (Khedezla), desvenlafaxine succinate (Pristiq), duloxetine (Cymbalta), levomilnacipran (Fetzima), and venlafaxine (Effexor); tetracyclic antidepressants of noradrenergic and specific serotonergic antidepressants (NaSSAs), such as Remeron; tricyclic antidepressants, such as Elavil, imipramine (Tofranil), nortriptyline (Pamelor), and Sinequan; monoamine oxidase inhibitors (MAOIs), such as isocarboxazid (Marplan), phenelzine (Nardil), selegiline (EMSAM), and tranylcypromine (Parnate); and benzodiazepines, such as sertraline (Xanax), diazepam (Valium), buspirone (Buspar), and lorazepam (Ativan). These drugs do carry a risk of addiction, tolerance, loss of effectiveness, inciting violent or self-destructive actions, fatigue, and drowsiness along with nausea, increased appetite and weight gain, loss of sexual desire and other sexual problems, insomnia, dry mouth, blurred vision, and so on.

Clinically, new treatments for MDD, GAD, MCD and PDD are urgently needed that are significantly more effective, have fewer side effects, and can be prescribed to a wider range of patients experiencing one or more psychiatric disorders, such as major depressive disorder, generalized anxiety disorder, mild chronic depression, premenstrual dysphoric disorder.

Inflammation can be defined as one of the immune responses for protecting living organisms from damage. The immune system can be triggered by various factors such as pathogens, damage to cells, and stress that may induce acute or chronic inflammatory responses in organs including the brain, potentially leading to tissue damage or disease. The latest advancements in neurobiological research provide increasing evidence that inflammatory and neurodegenerative pathways play a relevant role in insomnia. Preclinical and clinical studies on insomnia highlighted an increased production of inflammatory markers, such as interleukin (IL)-1, IL-6, tumor necrosis factor (TNF)-$\alpha$ and interferon (INF)-$\alpha$ and $\gamma$, and overactivated inflammatory signaling pathways including nuclear factor kappa B (NF-$_K$B). More recent studies have shown that blocking the biological actions of the cytokines IL-1 and TNF resulted in a reduction of physiological NREM sleep amount or NREM sleep rebound after sleep deprivation. On the other hand, increasing the availability of those cytokines promoted NREM sleep amount and intensity and suppressed REM sleep amount. These findings established both cytokines, IL-1 and TNF, as substances involved in the homeostatic regulation of sleep. Other cytokines, including IFN, IL-2, IL-4, IL-6, IL-10, IL-13, IL-15, and IL-18 also appear to have some sleep regulatory properties. The anti-inflammatory cytokines IL-4, IL-10, and IL-13 have been reported to attenuate NREM sleep amount in rabbits, while the pro-inflammatory acting cytokines IFN-γ, IL-2, IL-6, IL-15, and IL-18 have NREM sleep-promoting actions in animal models.

Ebastine is a second-generation H1-receptor antagonist and administered orally once-daily and is indicated for the treatment of the symptoms of allergic rhinitis and chronic idiopathic urticaria. In addition to blocking the H1-receptor, ebastine has other effects that contribute to its antiallergy effects. In vitro and in vivo studies, as well as clinical trials, the effects of ebastine on various mediators of inflammation have been shown. Ebastine significantly inhibits the anti-IgE-induced release of prostaglandin D2 (PGD2) and leukotrienes C4/D4 (LTC4/D4). Ebastine also inhibited the release of cytokines, including granulocyte-macrophage colony-stimulating factor (GM-CSF), tumour necrosis factor-a and interleukin-8. Its metabolite, carebastine, inhibits the release of PGD2.

Alprazolam is one of the most widely prescribed benzodiazepines for the treatment of generalized anxiety disorder and panic disorder. The neurochemical mechanism for alprazolam's anxiolytic effects is not fully understood but research shows that alprazolam enhances central nervous system GABAergic pre- and postsynaptic inhibition. Also, alprazolam binds both GABA and benzodiazepine receptors, each of which has both GABA and benzodiazepine recognition sites and GABA and related agents enhance the specific binding of benzodiazepine. Alprazolam may thus exert therapeutic anxiolytic effects via interaction with a high-affinity binding site on brain receptors. These benzodiazepine receptors interact with GABA receptors, potentiating GABAs synaptic inhibitory effect. We hypothesize that alprazolam's effects of nervous system GABAergic pre- and postsynaptic inhibition through GABA and benzodiazepine receptors stabilize the anti-inflammatory cytokines IL-4, IL-10, and IL-13. Alprazolam's antidepressant effects rest on its effect on $^3$H-DHA binding, indicating an ability to decrease beta adrenergic receptor sensitivity, specifically when given chronically at higher doses. Studies have shown that alprazolam significantly decreases the length of REM periods and frequency of REM burst activities as well as increases REM latency. We believe a differential effect of alprazolam versus other benzodiazepines on REM latency is of potential clinical importance.

Therefore, a unique combination of ebastine with alprazolam would potentially be, in terms of working through multi-mechanisms of actions, more effective in the treatment of major depressive disorder, generalized anxiety disorder, mild chronic depression, and premenstrual dysphoric disorder.

The present invention includes a pharmaceutical composition that comprises at least two active pharmaceutically active ingredients. This pharmaceutical composition comprises the first active ingredient that is ebastine and the second active ingredient that is alprazolam. If desired, the composition can include only ebastine and alprazolam as pharmaceutically active ingredients, e.g., the composition can consist of only ebastine and alprazolam as pharmaceutically active ingredients. Pharmaceutically inactive materials such as excipients may also be present in the pharmaceutical composition.

In some embodiments of this invention, ebastine in the pharmaceutical composition is provided in an amount of about 10 mg to about 30 mg and alprazolam in an amount of about 0.5 mg to about 5 mg.

The present invention also includes an oral pharmaceutical dosage form of the pharmaceutical composition that is a solid, liquid, or gel form. The oral pharmaceutical dosage form can include only ebastine and alprazolam as pharmaceutically active ingredients. For example, the oral pharmaceutical dosage form can consist of only ebastine and alprazolam as pharmaceutically active ingredients, e.g., only ebastine and alprazolam optionally in combination with non-pharmaceutically active materials such as excipients, binders, etc.

The present invention further includes use of the composition, such as by oral dosage, through administration to patients having no sleeping disorder but with one or more psychiatric disorders of major depressive disorder, generalized anxiety disorder, mild chronic depression, premenstrual dysphoric disorder.

In some embodiments of this invention, an oral pharmaceutical dosage form of the pharmaceutical composition containing ebastine in an amount of about 10 mg to about 30 mg and alprazolam in an amount of about 0.5 mg to about 5 mg is administered to patients with one or more psychiatric disorders, such as major depressive disorder, generalized anxiety disorder, mild chronic depression, premenstrual dysphoric disorder but the patients having no sleeping disorders.

Aspect 1 is a method comprising administering a pharmaceutical composition to a patient having no sleeping disorder such as insomnia; wherein the pharmaceutical composition comprises effective amounts of ebastine and alprazolam; and wherein the effective amounts together are sufficient to treat the patient with one or more psychiatric disorders, such as major depressive disorder, generalized anxiety disorder, mild chronic depression, premenstrual dysphoric disorder.

Aspect 2 is the method of Aspect 1, wherein the pharmaceutical composition is administered once or twice a day, or once every 2 or 3 or 4 days to the patient in an oral solid or liquid form or a gel form.

Aspect 3 is the method of any of Aspects 1-2, wherein the ebastine is present in the pharmaceutical composition in an amount in the range of about 10 mg to about 30 mg.

Aspect 4 is the method of any of Aspects 1-3, wherein the alprazolam is present in the pharmaceutical composition in an amount in the range of about 0.5 mg to about 5 mg.

Aspect 5 is the method of any of Aspects 1-4, wherein the ebastine is present in the pharmaceutical composition in an amount in the range of about 10 mg to about 20 mg.

Aspect 6 is the method of any of Aspects 1-5, wherein the alprazolam is present in the pharmaceutical composition in an amount in the range of about 1 mg to about 3 mg.

Aspect 7 is the method of any of Aspects 1-6, wherein: the ebastine is present in the pharmaceutical composition in an amount in the range of about 10 mg to about 20 mg; and the alprazolam is present in the pharmaceutical composition in an amount in the range of about 1 mg to about 3 mg.

Aspect 8 is the pharmaceutical composition of any of Aspects 1-7, wherein the pharmaceutical composition is formulated as an oral pharmaceutical dosage form.

Aspect 9 is the pharmaceutical composition of any of Aspects 8, wherein the oral pharmaceutical dosage form is a solid form or a liquid form or a gel form.

In another aspect, use of a combination of ebastine and alprazolam to treat one or more of major depressive disorder, generalized anxiety disorder, mild chronic depression, or premenstrual dysphoric disorder is described. In certain embodiments, the use includes administration of the combination of ebastine and alprazolam once or twice a day, or once every 2 or 3 or 4 days to the patient in an oral solid or liquid form or a gel form. In other embodiments, the use includes administration of the ebastine is present in the pharmaceutical composition in an amount in the range of about 10 mg to about 30 mg. In some embodiments, the use includes administration of the alprazolam in the pharmaceutical composition in an amount in the range of about 0.5 mg to about 5 mg. In some embodiments, the use includes administration of the ebastine in the pharmaceutical composition in an amount in the range of about 10 mg to about 20 mg. In further embodiments, the use includes administration of the alprazolam in the pharmaceutical composition in an amount in the range of about 1 mg to about 3 mg. In certain embodiments, the use include administration of the ebastine in the pharmaceutical composition in an amount in the range of about 10 mg to about 20 mg, and administration of the alprazolam is the pharmaceutical composition in an amount in the range of about 1 mg to about 3 mg. In additional embodiments, the use includes administration of the pharmaceutical composition as an oral pharmaceutical dosage form. In other embodiments, the use includes administration of the oral pharmaceutical dosage form in a solid form or a liquid form or a gel form.

DETAILED DESCRIPTION

Through clinical practices, the inventors of the present invention found that a pharmaceutical composition with oral dosage forms comprising the active agents, ebastine and alprazolam, is suitable for treating patients, e.g., humans, suffering from one or more psychiatric disorders, such as major depressive disorder, generalized anxiety disorder, mild chronic depression, premenstrual dysphoric disorder. A pharmaceutical composition with oral dosage forms comprising the active agents, ebastine and alprazolam, is also suitable for treating patients, e.g., humans, suffering from one or more psychiatric disorders, such as major depressive disorder, generalized anxiety disorder, mild chronic depression, or premenstrual dysphoric disorder where the patients have no sleeping disorders such as, for example insomnia.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Figure 1:
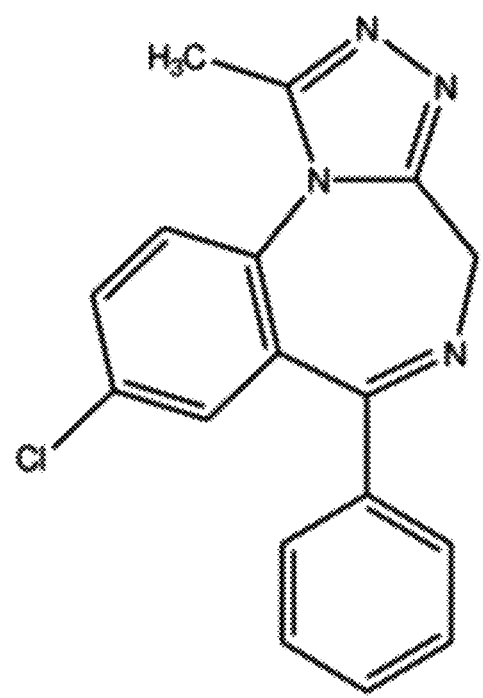
FIG. 1 shows a chemical structure of alprazolam.

As used herein, the term "alprazolam" refers to 8-chloro-1-methyl-6-phenyl-4H-s-triazolo[4,3-a][1,4]benzodiazepine as shown in FIG. 1.

Figure 2:
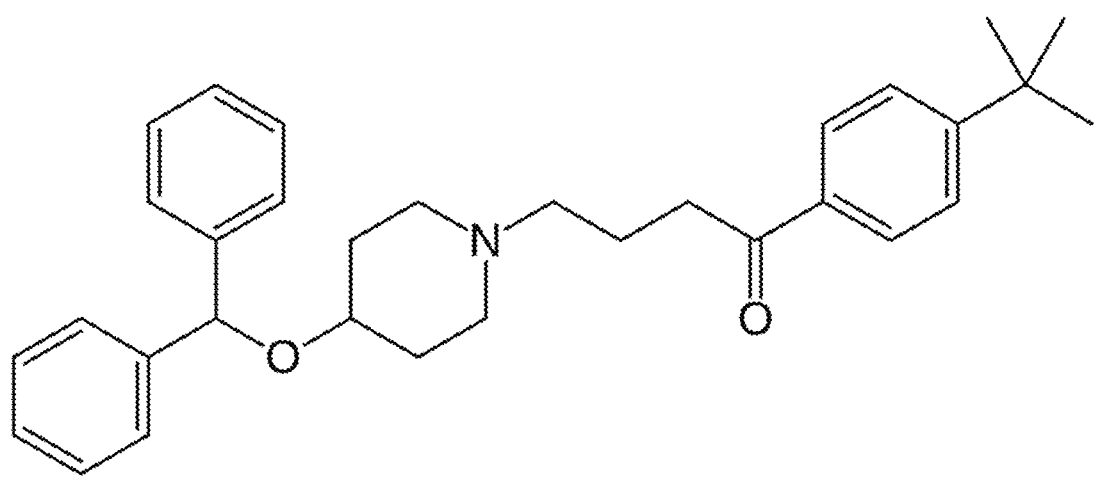
FIG. 2 shows a chemical structure of ebastine.

As used herein, the term "ebastine" refers to 4-diphenylmethoxy-1-[3-(4-tert-butylbenzoyl)-propyl]piperidine as shown in FIG. 2.

As used herein, "treating" or "treatment" means complete cure or incomplete cure, or it means that the symptoms of the underlying disease or associated conditions are at least reduced and/or delayed, and/or that one or more of the underlying cellular, physiological, or biochemical causes or mechanisms causing the symptoms are reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to a mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be by way of any one or more of capsule, tablet, gel, spray, drops, solution, suspensions, syrups, or the like.

The term "about" used herein in the context of quantitative measurements means the indicated amount +10%. For example, with a +10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (by Loyd Allen, 2013) and Handbook of Pharmaceutical Manufacturing Formulations (Volumes 1-6 by Sarfaraz K. Niazi). Accordingly, incorporation of the active compounds and a controlled, or slow release matrix may be implemented.

Either fluid or solid unit dosage forms can be readily prepared for oral administration, for example, admixed with any one or more of conventional ingredients such as dicalcium phosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. In older or incoherent subjects sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure can be typically administered orally. This disclosure therefore provides pharmaceutical compositions that comprise a solid dispersion comprising ebastine and alprazolam as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (by Loyd Allen, 2013) and Handbook of Pharmaceutical Manufacturing Formulations (Volumes 1-6 by Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into tablets, tablets may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed. In embodiments, the pharmaceutical compositions are formulated as tablets, caplets, pills, or capsules for gastrointestinal absorption, such as formulated to be capable of delaying disintegration until the pharmaceutical composition is in the gastrointestinal tract of a patient. In embodiments, delaying disintegration is achieved using a coating.

In embodiments, the pharmaceutical compositions can comprise synergistically effective amounts of ebastine and alprazolam, such as a) about 10 mg to 30 mg of ebastine and b) about 0.5 mg to 5 mg of alprazolam or a) about 10 mg to 20 mg of ebastine and b) about 0.5 mg to 3.0 mg of alprazolam or a) about 10 mg to 15 mg of ebastine and b) about 1.0 mg to 3.0 mg of alprazolam, or any amount of ebastine or alprazolam within these ranges. In embodiments, the alprazolam is present in the pharmaceutical composition in a synergistically effective amount relative to the amount of ebastine and can include pharmaceutical compositions comprising a) about up to and including any of 0.5 mg, 1 mg, 1.5 mg, 2 mg, 2.5 mg, 3 mg, 3.5 mg, 4 mg, 4.5 mg, 5 mg or any amount within any of these ranges and b) about up to and including any of between 0.5 mg, 5 mg alprazolam, or any amount within any of these ranges. For example, the compositions comprising synergistically effective amounts of ebastine and alprazolam can comprise a) about 10 mg of ebastine and b) about 1.0 mg of alprazolam. Further, for example, compositions of the invention can comprise ebastine present in an amount in the range of about 10 mg to about 30 mg and a synergistically effective amount of alprazolam in an amount in the range of about 0.5 mg to about 5 mg. In embodiments, the synergistically effective amounts can be such that the amount of ebastine present in the composition can be equal to or more than the amount of alprazolam present in the composition. In embodiments, the synergistically effective amounts are such that the ebastine is present in the pharmaceutical composition in an amount of at least 10 mg and alprazolam is present in an amount of at least 0.5 mg. Any one or more of the compositions of the invention can be used with any one or more the methods of the invention disclosed herein, or other methods of using the compositions.

It will be understood, that the amount of the pharmaceutical composition containing ebastine and alprazolam actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing ebastine and alprazolam as described herein are administered to a patient suffering from a psychiatric disorder, by administration (such as oral administration) once daily, twice daily, up to four times a day, once every other day, once a week, two times a week, three times a week, four times a week, or five times a week, or combinations thereof. The pharmaceutical compositions, pharmaceutical dosage forms, and tablets containing ebastine and alprazolam as described herein are administered to a patient suffering from a psychiatric disorder (but not a sleeping disorder), by administration (such as oral administration) once daily, twice daily, up to four times a day, once every other day, once a week, two times a week, three times a week, four times a week, or five times a week, or combinations thereof.

In embodiments, patients are administered the pharmaceutical composition(s) with a therapeutic effective daily dosage of ebastine in the range of about 10 mg to about 30 mg and alprazolam in an amount in the range of about 0.5 mg to about 5 mg.

In embodiments, the pharmaceutical dosage forms and tablets of pharmaceutical compositions containing ebastine, such as ebastine and alprazolam as described herein are effective in reversing, reducing, alleviating, and/or treating one or more psychiatric disorders, such as major depressive disorder, generalized anxiety disorder, mild chronic depression, or premenstrual dysphoric disorder but the patients having no sleeping disorders, in about 1-8 weeks, such as within 1, 2, 3, 4, 5, 6, 7, or 8 weeks, or any range in between.

The following Examples are illustrative and should not be interpreted to limit the scope of the claimed subject matter.

Example 1

A 34-year-old female patient was diagnosed with generalized anxiety disorder (GAD) and she had no complaints of having insomnia. She was prescribed with alprazolam 0.5 mg for 2 weeks during the first clinic visit, but she reported no improvement from the treatment. Then the patient was prescribed with alprazolam 2 mg for 2 weeks during the second clinic visit but she had no improvement. Then she was treated with the combination of ebastine (20 mg) and alprazolam (1 mg) for 2 weeks. By the end of the treatment with the combination, the patient reported 50% improvement in her anxiety symptom of persistent worry, headaches, irritability, nervousness and low energy without any complain of side effects. With a continued treatment of the same combination for 4 more weeks, she reported no symptoms of GAD. The inventors believe the composition of two mechanisms of actions provided a new solution for treating her GAD which could not be treated with alprazolam and the like alone.

Example 2

A 55-year-old male patient having no insomnia symptom was diagnosed with major depressive disorder (MDD) showing persistent sadness, loneliness, helpless, and hapless. After failed treatments with two anti-depressants duloxetine and bupropion, the patient was prescribed with alprazolam 5 mg for 2 weeks but showed no improvement. Then he was prescribed with a combination of ebastine (30 mg) and alprazolam (5 mg) for 4 weeks. By the end of the 2nd week of his treatments, he reported the improvement of his MDD symptoms by 50%. By the end of the 4th week of his treatments, he had no symptoms of MDD. In this case, the composition of two mechanisms of actions provided a new solution for treating his MDD which could not be treated with other options, such traditional SSRIs and the like alone.

Example 3

A 57-year-old male patient with no insomnia symptom was having allergic rhinitis with itchy nose, mouth and eyes, frequent sneezing, watery eyes and coughing, and runny nose when he was diagnosed with mild chronic depression (MCD) but showing symptoms of sadness, lack of interest, loneliness and helpless, consistent frustration for 4 weeks with failed treatment history of allergic rhinitis. The patient was prescribed with ebastine 30 mg for 3 weeks from the first clinic visit. During the second clinic visit, he reported a complete recovery from allergic rhinitis showing no symptoms of itchy nose, mouth and eyes, frequent sneezing, watery eyes and coughing, and runny nose. But his symptoms from MCD were persistent. He was prescribed with alprazolam 1 mg for 3 weeks from the second clinic visit but no improvement from those symptoms was reported. Then he was prescribed with a combination of ebastine (10 mg) and alprazolam (0.5 mg) for a 4-week treatment. By the end of the treatment, he reported 90% improvement from his MCD symptoms with no intolerable side effects.

Example 4

A 47-year-old male patient with no insomnia symptom was diagnosed with major depressive disorder (MDD) with persistent sadness, lack of interest, and feeling lonely. Both of his previous treatments with bupropion and fluoxetine failed to improve his symptoms from MDD. He was prescribed with alprazolam 5 mg for 2 weeks during his first clinic visit but he reported 20% improvement from the treatment. Then he was treated with a combination of ebastine (30 mg) and alprazolam (0.5 mg) for 4 weeks from the second clinic visits. By the end of his treatments, he reported a complete recovery from MDD symptoms. In this case, the composition of two mechanisms of actions provided a new solution for treating his MDD which could not be treated with other options.

Example 5

A 51-year-old female patient with no insomnia symptom order was diagnosed with GAD. The patient was treated with alprazolam (2 mg) for 2 weeks from her first clinic visit and alprazolam (4 mg) for 2 weeks from her second clinic visit. But both treatments failed to improve her symptoms of her persistent anxiety, agitation, sweating, nausea, and headaches. On the third clinic visit, the patient was prescribed with the combination of ebastine (10 mg) and alprazolam (4 mg). By the end of the treatment, the patient reported about 90% improvement of her symptoms with no complain of intolerable side effects. The inventors believe that the two compositions of two mechanisms of actions provided a new solution for treating her MDD which could not be treated with other options.

Example 6

A 34-year-old female patient with no insomnia symptom was diagnosed with premenstrual dysphoric disorder (PDD) with symptoms of persistent hopelessness, sadness, anxiety and frequent tearfulness on the first clinic visit and was provided with fluoxetine 40 mg for 3 weeks. But no improvement was reported. The patient was treated with alprazolam (2 mg) for 2 weeks on the second clinic visit but the treatments failed to improve her symptoms. Then the patient was prescribed with the combination of ebastine (20 mg) and alprazolam (2 mg) for 2 weeks. At the end of the 2-week treatment with the composition, she reported about 60% improvement of her symptoms. After a continued treatment with the same composition for 4 more weeks, the patient reported no major symptoms of PDD. The inventors believe the composition of two mechanisms of actions provided a new solution for treating her PDD which could not be treated with other options.

REFERENCES

P. Van Cauwenberge, T. De Belder & Lien Sys, "A review of the second-generation antihistamine eszopiclone ebastine for the treatment of allergic disorders". Expert Opinion on Pharmacotherapy, 2004; 5:8, 1807-1813.

Rosenblat J D, Kakar R, Mcintyre R S, 2015. Int J Neuropsychopharmacol, The Cognitive Effects of Antidepressants in Major Depressive Disorder: A Systematic Review and Meta-Analysis of Randomized Clinical Trials. July 25;19 (2).

Ruihua Hou, 2017, Peripheral inflammatory cytokines and immune balance in Generalized Anxiety Disorder: case-controlled study. Brain Behav Immun. 2017 May; 62:212-218.

Michelle Guignet, 2020, Persistent behavior deficits, neuroinflammation, and oxidative stress in a rat model of acute organophosphate intoxication, Vol 133, January 2020, 104431.

J. Sastre, "Ebastine in allergic rhinitis and chronic idiopathic urticaria". Current Topics in Med. Chem. 2011, 11:221-240.

L. Wiserman and D. Faulds, "Ebastine, A Review of its Pharmacological Properties and Clinical Efficacy in the Treatment of Allergic Disorders". Drugs 1996, 51 (2): 260-277.

Mónica de la Peña Bravo, L. D. Serpero, et al, "Inflammatory proteins in patients with obstructive sleep apnea with and without daytime sleepiness". Sleep Breath, 2007 September;11 (3): 177-85.

R. Nadeem, J. Molnar, et al., "Serum inflammatory markers in obstructive sleep apnea: a meta-analysis", Journal of Clinic Sleep Med (2013) October 15; 9 (10): 1003-12.

J. Gaines, A. N. Vgontzas, et al, "Inflammation mediates the association between visceral adiposity and obstructive sleep apnea in adolescents" Am J. Physiol. Endocrinol Metab., 2016 Nov. 1; 311 (5).

A Kales, E O Bixler, et al., "Alprazolam: effects on sleep and withdrawal phenomena" J Clin Pharmacol. 1987, 27 (7): 508-15

A. Kales, CR. Soldatos, et al.,"Diazepam: effects on sleep and withdrawal phenomena" J Clin Psychopharmacol. 1988, 8 (5): 340-6.

E. B. Mohns, "Discontinuation and withdrawal problems of alprazolam" West J Med. 1989,151 (3): 312

Loyd Allen, Ansel's Pharmaceutical Dosage Forms and Drug Delivery Systems, Tenth (2013).

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

What is claimed is:

1. A method of treating one or more psychiatric disorders selected from the group consisting of major depressive disorder, generalized anxiety disorder, mild chronic depression, premenstrual dysphoric disorder and symptoms thereof to a patient, comprising administering a pharmaceutical composition comprising ebastine and alprazolam, wherein the ebastine and the alprazolam are present in the pharmaceutical composition in synergistically effective amounts.

2. The method of claim 1, wherein the patient has no sleeping disorder such as insomnia thereof.

3. The method of claim 1, wherein the pharmaceutical composition is administered to the patient in an oral solid or liquid form.

4. The method of claim 1, wherein the ebastine is present in the pharmaceutical composition in an amount in the range of about 10 mg to about 30 mg.

5. The method of claim 1, wherein the alprazolam is present in the pharmaceutical composition in an amount in the range of about 0.5 mg to about 5 mg.

6. The method of claim 5, wherein the alprazolam is present in the pharmaceutical composition in an amount in the range of about 0.5 mg to about 3 mg.

7. A pharmaceutical composition for use in treating one or more psychiatric disorders selected from the group consisting of major depressive disorder, generalized anxiety disorder, mild chronic depression, premenstrual dysphoric disorder and one or more symptoms thereof, wherein the pharmaceutical composition comprises ebastine and alprazolam wherein the ebastine and the alprazolam are present in the pharmaceutical composition in synergistically effective amounts.

8. The pharmaceutical composition of claim 7, wherein the pharmaceutical composition is formulated as an oral pharmaceutical dosage form.

9. The pharmaceutical composition of claim 7, wherein the oral pharmaceutical dosage form is a solid form or a liquid form or a gel form.

10. A pharmaceutical composition comprising ebastine and alprazolam for use in the treatment of a psychiatric disorder wherein the ebastine and the alprazolam are present in the pharmaceutical composition in synergistically effective amounts.

11. The pharmaceutical composition of claim 10, wherein the psychiatric disorder is selected from the group consisting of major depressive disorder, generalized anxiety disorder, mild chronic depression, and premenstrual dysphoric disorder.

12. The pharmaceutical composition of claim 10, wherein the pharmaceutical composition is administered to the patient in an oral solid or liquid form.

13. The pharmaceutical composition of claim 10, wherein the ebastine is present in the pharmaceutical composition in an amount in the range of about 10 mg to about 30 mg.

14. The pharmaceutical composition of claim 10, wherein the alprazolam is present in the pharmaceutical composition in an amount in the range of about 0.5 mg to about 5 mg.

15. The pharmaceutical composition of claim 10, wherein the alprazolam is present in the pharmaceutical composition in an amount in the range of about 0.5 mg to about 3 mg.

16. The pharmaceutical composition of claim 10, wherein the subject does not have a sleeping disorder.

17. The pharmaceutical composition of claim 16, wherein the psychiatric disorder is selected from the group consisting of major depressive disorder, generalized anxiety disorder, mild chronic depression, and premenstrual dysphoric disorder.

18. The pharmaceutical composition of claim 16, wherein the pharmaceutical composition is administered to the patient in an oral solid or liquid form.

* * * * *